US005591201A

United States Patent [19]
Lam

[11] Patent Number: 5,591,201
[45] Date of Patent: Jan. 7, 1997

[54] METHOD AND APPARATUS FOR HAEMOSTATIC COMPRESSION

[76] Inventor: Anthony H. Lam, 10151 - 74 Street NW., Edmonton, Alberta, Canada, T6A 2X8

[21] Appl. No.: 332,767

[22] Filed: Nov. 1, 1994

[51] Int. Cl.⁶ .................................................. A61B 17/12
[52] U.S. Cl. ................................ 606/201; 5/658
[58] Field of Search ...................... 606/151, 157, 606/158, 201, 203; 5/503, 658, 659; 294/67.2, 119.1

[56] References Cited

U.S. PATENT DOCUMENTS

| | | | |
|---|---|---|---|
| 1,887,022 | 11/1932 | Hoffman et al. | 606/203 X |
| 3,096,975 | 8/1963 | Irwin | 269/169 |
| 3,221,349 | 12/1965 | Bradley | 5/658 |
| 3,261,034 | 7/1966 | Bradley | 5/658 |
| 4,220,322 | 9/1980 | Hobday | 269/6 |
| 4,373,709 | 2/1983 | Whitt | 606/203 X |
| 4,874,155 | 10/1989 | Goul | 269/6 |
| 4,926,722 | 5/1990 | Sorensen et al. | 81/487 |
| 4,966,340 | 10/1990 | Hunter | 5/503.1 X |
| 5,022,137 | 6/1991 | Sorensen et al. | 29/559 |
| 5,123,909 | 6/1992 | LeVeen et al. | 606/201 |
| 5,129,916 | 7/1992 | Buonafede | 606/201 |
| 5,133,734 | 7/1992 | Lee | 606/201 |
| 5,139,512 | 8/1992 | Dreiling | 606/201 |
| 5,269,803 | 12/1993 | Geary et al. | 606/201 |
| 5,295,996 | 3/1994 | Blair | 606/203 |
| 5,301,683 | 4/1994 | Durkan | 606/201 X |
| 5,304,201 | 4/1994 | Rice | 606/201 |
| 5,319,816 | 6/1994 | Ruehl | 5/600 |

FOREIGN PATENT DOCUMENTS

| | | | |
|---|---|---|---|
| 1208094 | 6/1986 | Canada | A61B 17/04 |
| 1289030 | 9/1988 | Canada | A61B 17/02 |
| 2026687 | 4/1991 | Canada | A61B 17/12 |
| 2057296 | 6/1992 | Canada | A61B 17/12 |
| 2079277 | 4/1993 | Canada | A61B 17/12 |
| 2099301 | 12/1993 | Canada | A61B 17/12 |
| 2664807 | 7/1990 | France . | |
| 1408886 | 10/1975 | United Kingdom | B25B 27/00 |
| 1472278 | 5/1977 | United Kingdom | B25B 1/06 |
| 1516748 | 7/1978 | United Kingdom | B25B 9/00 |
| 1544156 | 4/1979 | United Kingdom | B25B 5/06 |
| 1555455 | 11/1979 | United Kingdom | F04B 9/14 |
| 2178689 | 2/1987 | United Kingdom | B25B 5/06 |
| 2204264 | 11/1988 | United Kingdom | B25B 5/06 |
| WO91/02492 | 3/1991 | WIPO | A61B 17/12 |

OTHER PUBLICATIONS

Brochure copyrighted in 1993 by Instromedix, Inc. Compressar System.

Primary Examiner—Michael H. Thaler
Assistant Examiner—Patrick W. Rasche

[57] ABSTRACT

The apparatus comprises a wheeled base, a vertical pole mounted on the base, and upper and lower, elongate, horizontal arms extending from the support member. The apparatus can be rolled up to a surgical bed so that the outer end of the upper arm is positioned over the patient on the bed and the outer end of the lower arm is located beneath the bed below the patient. Each arm is slidably mounted on the pole. Each arm carries quick-acting first means for disengagably locking the arm to the support member to prevent sliding movement and quick-acting second means for temporarily disengaging the first means and incrementally advancing the arm along the support member. Thus the arms can be quickly moved to bracket the patient and bed underside, then locked and advanced incrementally to clamp against the bed and patient. The apparatus is useful for clamping open arterial incisions to stop bleeding.

3 Claims, 6 Drawing Sheets

METHOD AND APPARATUS FOR HAEMOSTATIC COMPRESSION

FIELD OF THE INVENTION

The present invention relates to a method and apparatus for haemostatic compression for use on surgical floors of hospitals for applying a compression force to an artery.

BACKGROUND OF THE INVENTION

U.S. Pat. Nos. 5,133,734 and 5,304,201 most closely resemble haemostatic compression apparatus used on surgical floors of hospitals for applying a compression force to a femoral artery. These patents both have a baseboard, a post that extends vertically from the baseboard, and an arm that extends horizontally from the post to support an adjustable compression member. The patents teach that the baseboard should be placed under the hips of a supine-lying patient. The arm is then moved axially along the post to position the compression member. The compression member is then adjusted to provide a compression force against the femoral artery.

The problem with haemostatic compression apparatus as taught in the above described patent references is that they cannot be readily positioned by one staff member without the patient's cooperation in positioning his or her hips on the baseboard. If the patient is unconscious, too obese to lift his or her own weight or for some other reason unable to assist, at least two staff members are required. One staff member endeavours to lift the patient's hips and the other staff member position's the apparatus. This requires some coordinated effort by the staff members. More seriously, it results in delays in reapplying the haemostatic compression apparatus if a reoccurrence of bleeding is noticed by a nurse providing post-surgical care after the haemostatic compression apparatus has been removed and the medical team dispersed.

SUMMARY OF THE INVENTION

What is required is a method and apparatus for haemostatic compression that will allow for rapid deployment by one medical staff member.

According to one aspect of the present invention there is provided a method for haemostatic compression. Firstly, provide an elongate support member having a first end and a second end, a first arm movable axially along the support member, a second arm movable axially along the support member, and a haemostatic compression member secured to the first arm and oriented toward the second arm. Secondly, place the second end of the support member on a floor immediately adjacent to a bed containing a patient and move the second arm axially along the support member until the second arm engages an underside of the bed. Thirdly, move the first arm axially along the support member until the haemostatic compression member engages the patient and applies a compression force.

Using the method, as described, the haemostatic compression apparatus may be rapidly deployed. It is to be noted that the medical staff member need not lift the patient in any way. Instead of using a baseboard, as taught in the prior art, the second end of support member is positioned upon the floor with the second arm moved to a position where it bears against the underside of the surgical bed. According to another aspect of the invention, there is provided a floor-supported haemostatic compression apparatus for use with a patient supported on a generally horizontally extending bed, comprising: a wheel-supported base; a support member extending upwardly from the base and being of sufficient length to extend above the patient; upper and lower arms, each having inner and outer ends and being mounted at its inner end to the support member so as to be freely slidable therealong; the upper arm extending horizontally and having sufficient length so that its outer end may be positioned over the patient when the support member is adjacent the bed, said upper arm carrying a downwardly extending, haemostatic compression member at its outer end; the lower arm being generally L-shaped and comprising a horizontally extending first section and an upwardly extending second section, the first section having sufficient length so that the second section may be positioned beneath the patient, the second section having sufficient length to engage the underside of the bed while providing clearance of the first section relative to the bed; means, associated with the upper arm, for disengagably locking it to the support member to prevent sliding movement therealong; means, associated with the upper arm, for temporarily disengaging the upper arm locking means and incrementally advancing the upper arm downwardly along the support member; means, associated with the lower arm, for disengagably locking it to the support member to prevent sliding movement therealong.

The apparatus, as described, sets forth those aspects of the invention that are essential to follow the teachings of the described method. It is to be noted that, in contrast to the prior art, two axially movable arms are provided.

Although beneficial results may be obtained through the use of the haemostatic compression apparatus, as described above, it is preferable that the apparatus be capable of standing erect when not in use and that the apparatus be sufficiently stable that medical staff need not be concerned about the second end of the support member sliding out of position. Even more beneficial results may, therefore, be obtained when the second end of the support member forms a stable floor-positioned base. It is preferred that the base have a plurality of wheels with wheel locking means. This allows the base to be wheeled into position on the wheels and then the wheel locking means engaged to preclude further rotation of the wheels.

Although beneficial results may be obtained through the use of the haemostatic compression apparatus, as described above, it is important that the amount of compression force be carefully monitored. If the compression force applied is insufficient the bleeding will not be completely stopped; one the other hand, if the compression force is excessive the patient can be harmed. Even more beneficial results may, therefore be obtained when a gauge for measuring compressive force is coupled with the haemostatic compression member, whereby a reading of a compressive force exerted by the haemostatic compression member is obtained.

Although beneficial results may be obtained through the use of the haemostatic compression apparatus, as described above, the haemostatic compression apparatus must be capable of both rapid adjustment to place the apparatus in position before unacceptable blood loss occurs and also fine adjustment to control the amount of compression force exerted. Even more beneficial results may, therefore, be obtained when the means for locking the first arm in a selected position to the support member includes both a locking/release lever and an incremental adjustment lever. The locking/release lever permits the rapid positioning that is required. The incremental adjustment lever permits an incremental increase in compression force once the haemostatic compression member is in position.

Although beneficial results may be obtained through the use of the haemostatic compression apparatus, as described above, it is sometimes necessary to apply pressure to two adjacent puncture sites or to apply pressure to both an artery providing blood from the patient's heart to a limb and a vein through which blood from the limb returns to the heart. Even more beneficial results may, therefore, be obtained when the haemostatic compression member is generally arcuate and has a peripheral edge with a slot extending in from the peripheral edge.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
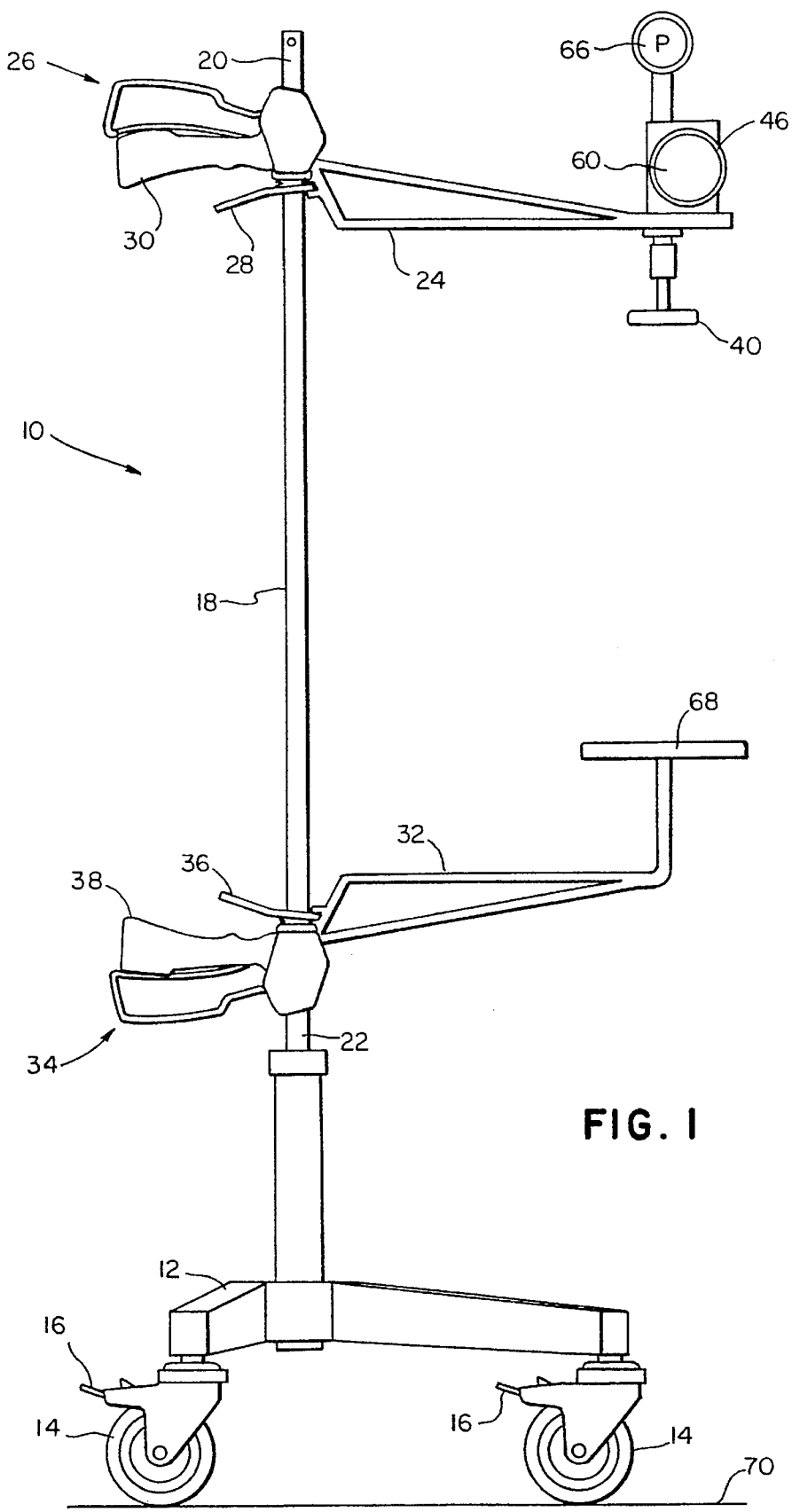
FIG. 1 is a side elevation view of a haemostatic compression apparatus constructed in accordance with the teachings of the present invention.

The preferred embodiment, a haemostatic compression apparatus generally identified by reference numeral 10, will now be described with reference to FIGS. 1 through 7.

Figure 2:
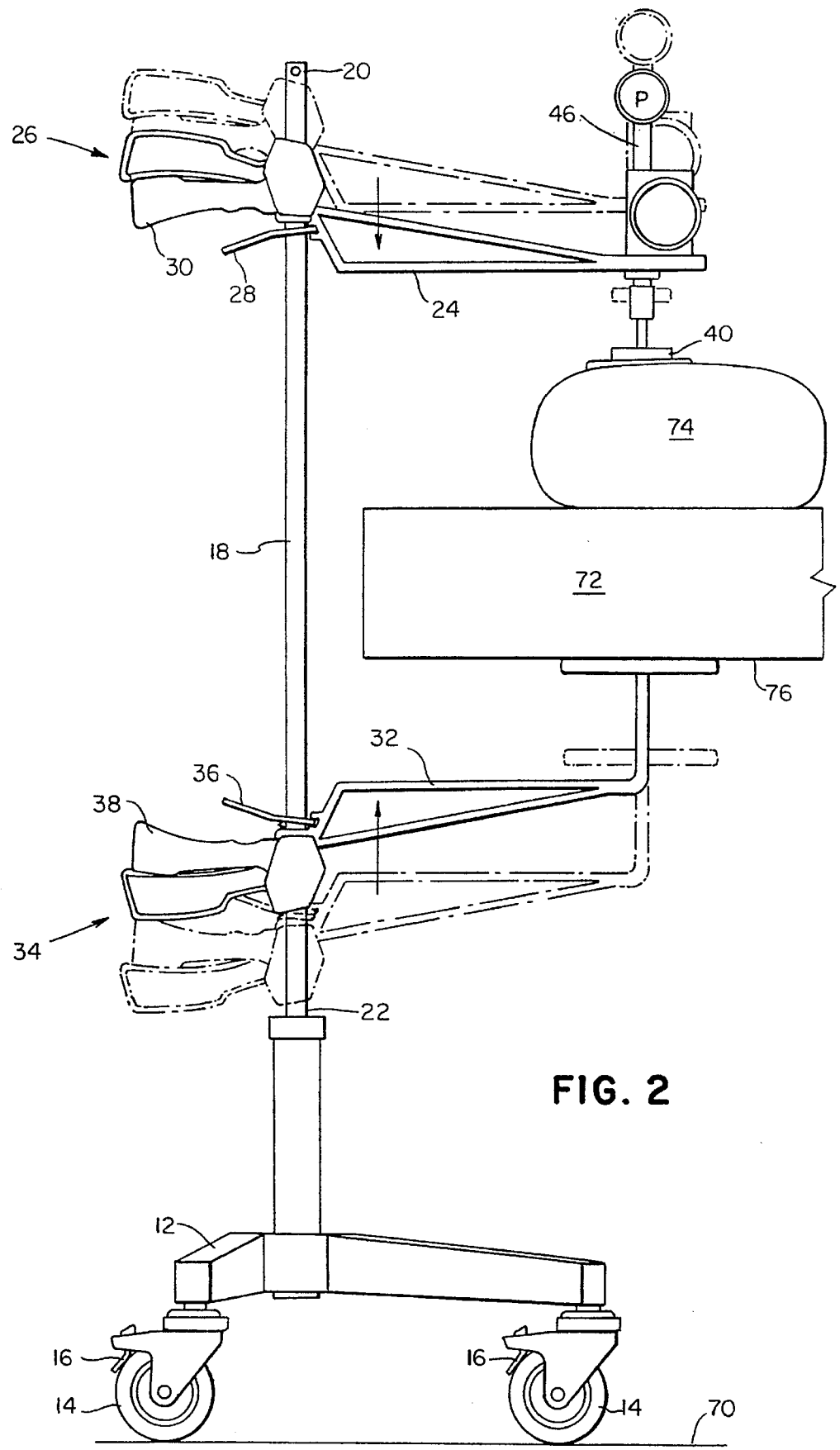
FIG. 2 is a side elevation view of the haemostatic compression apparatus illustrated in FIG. 1, in use applying a compression force to a patient in accordance with the teachings of the method.
Figure 3:
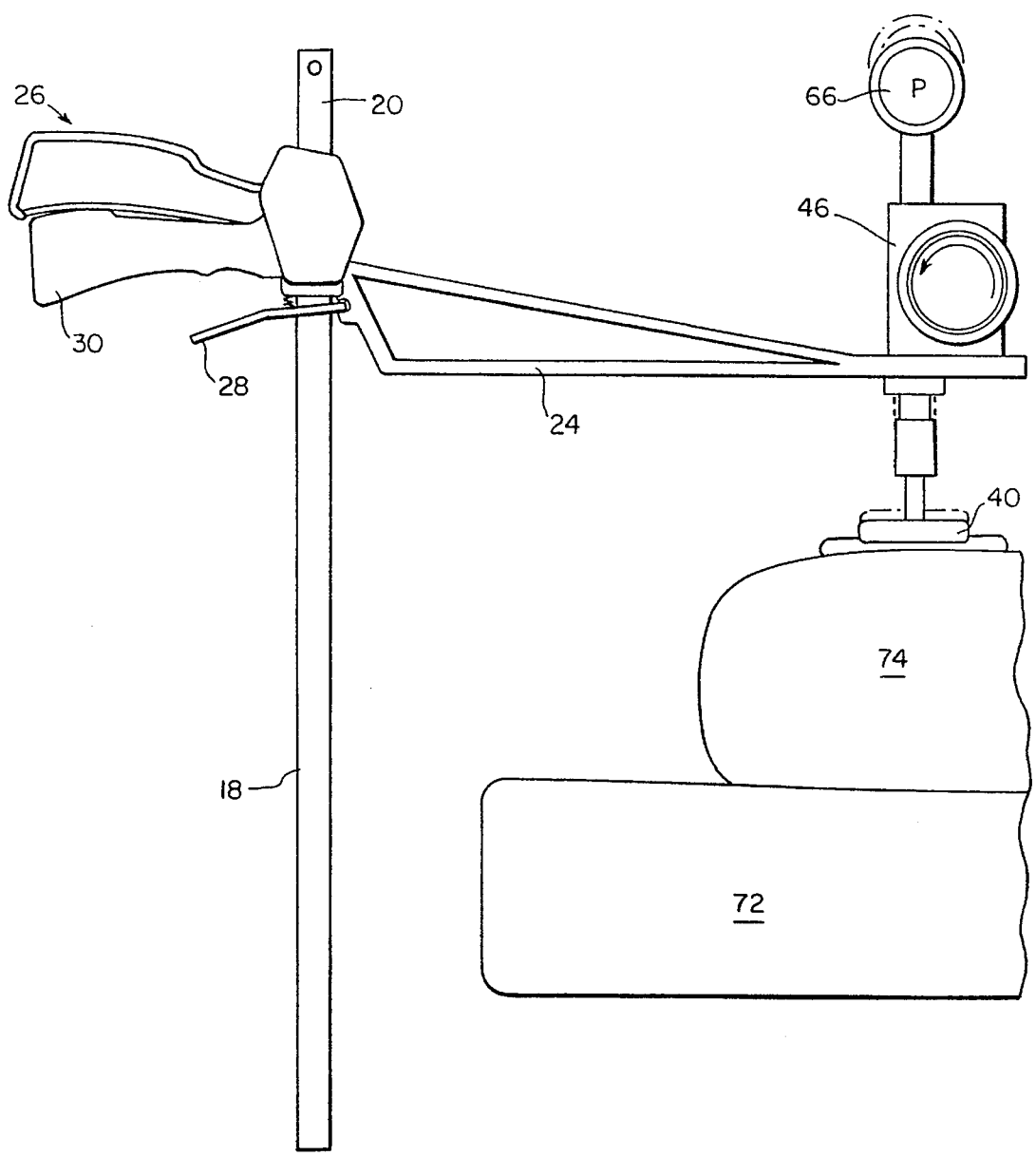
FIG. 3 is a detailed side elevation view of a portion of the haemostatic compression apparatus illustrated in FIG. 2.
Figure 4:
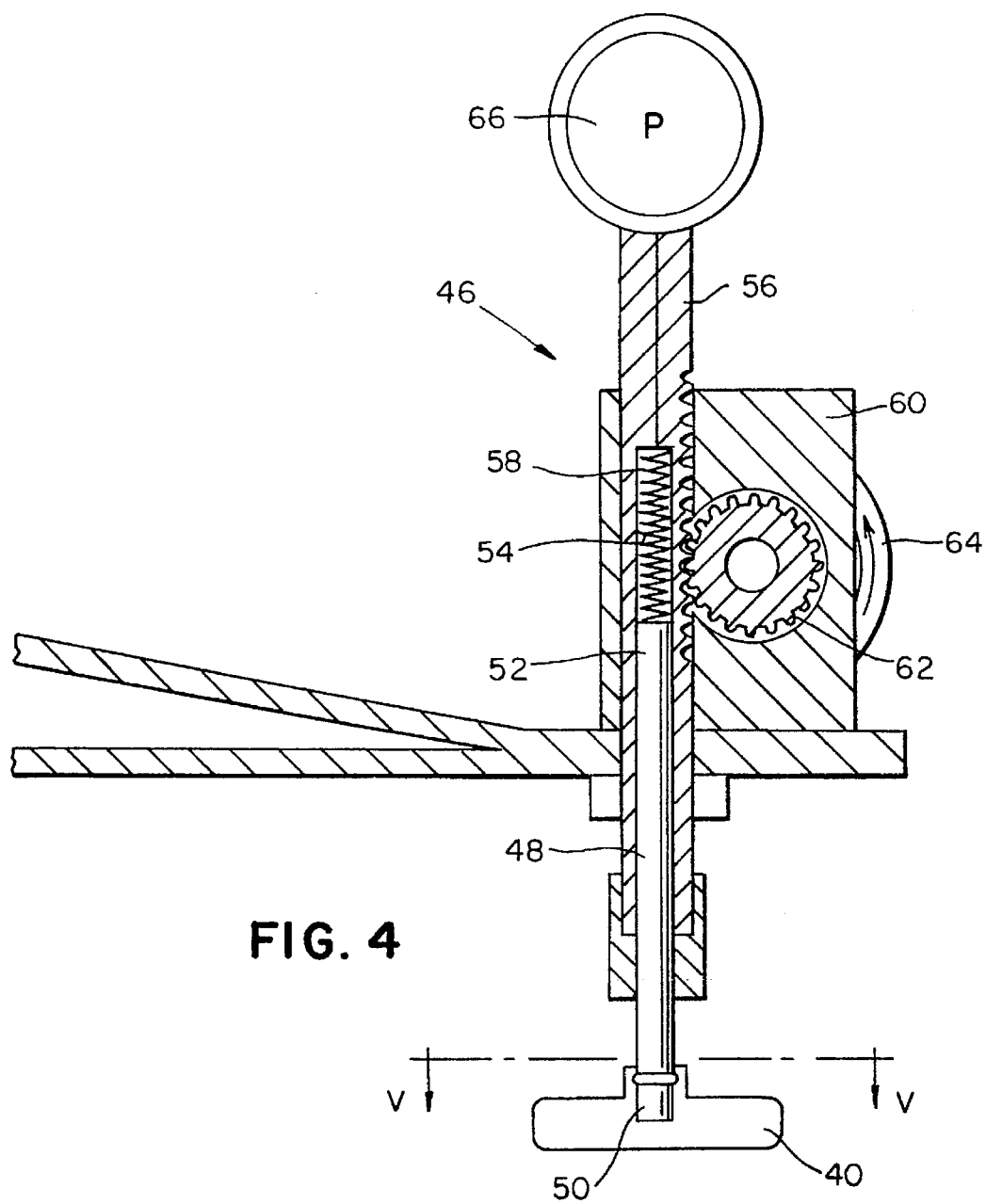
FIG. 4 is a detailed side elevation view in section of a gauge portion of the haemostatic compression apparatus illustrated in FIG. 3.
Figure 5:
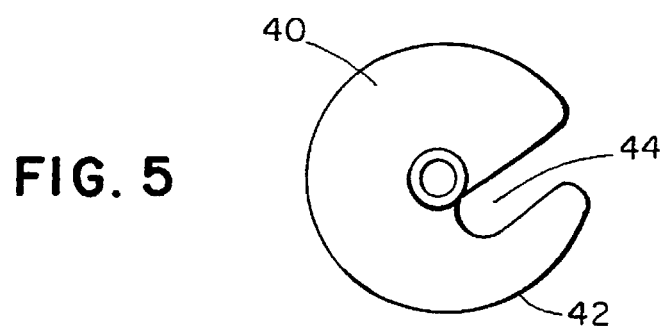
FIG. 5 is a section view taken along section lines V—V of FIG. 4.
Figure 6:
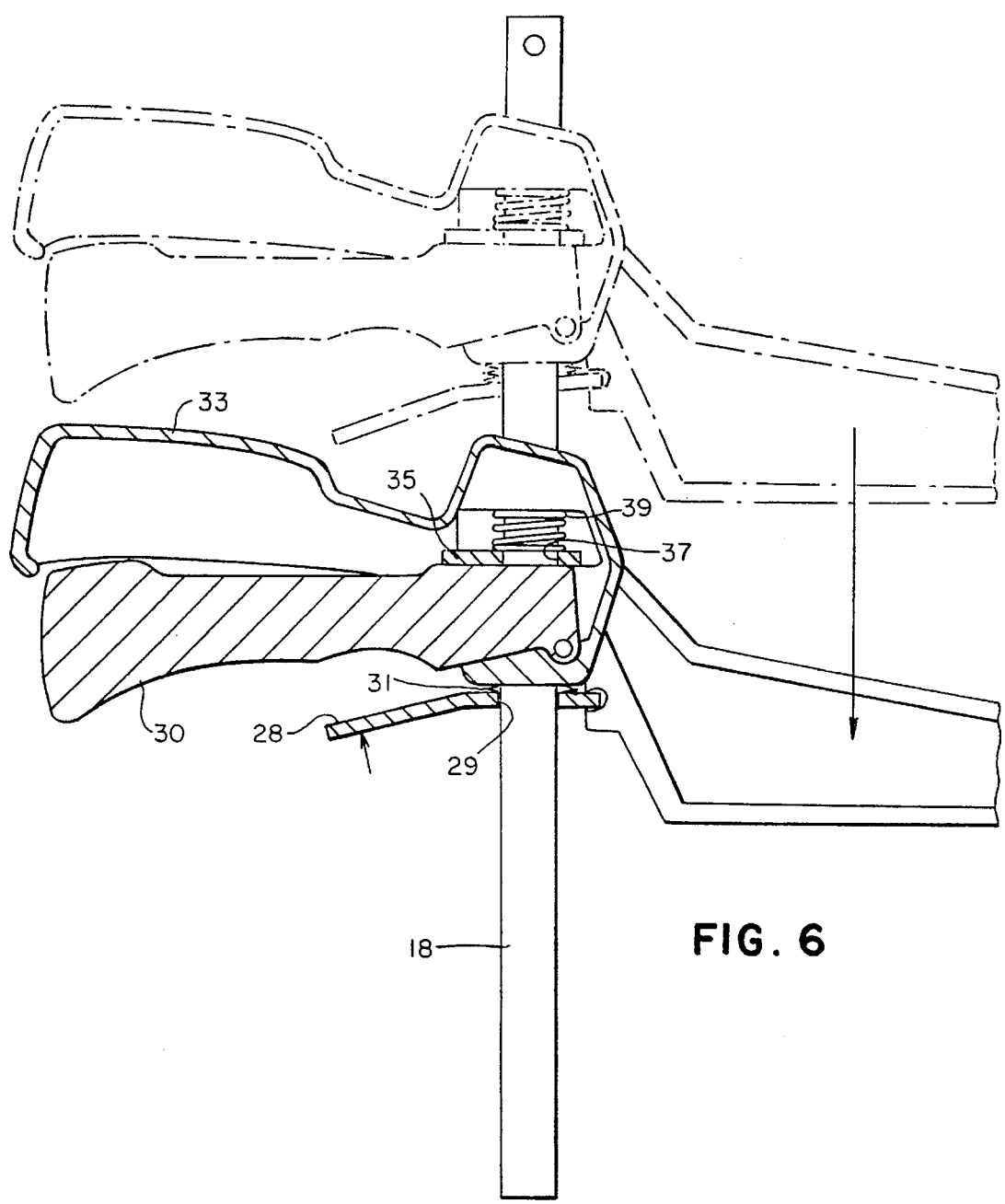
FIG. 6 is a detailed side elevation view in section of an arm locking portion of the haemostatic compression apparatus illustrated in FIG. 1.
Figure 7:
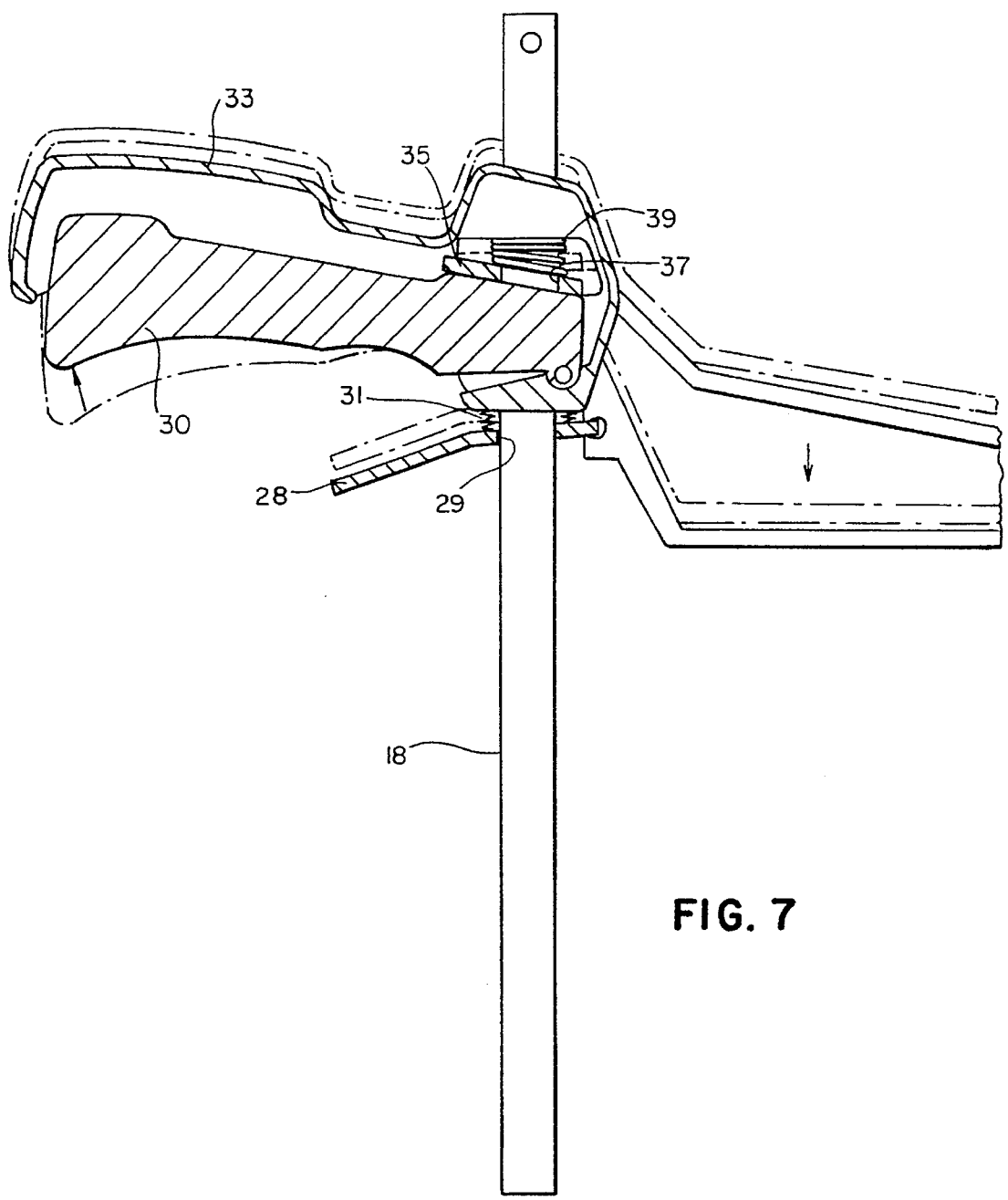
FIG. 7 is an alternate detailed side elevation view in section of the arm locking portion of the haemostatic compression apparatus illustrated in FIG. 1.

Referring to FIGS. 1 and 2, haemostatic compression apparatus 10 includes a stable base 12 having a plurality of floor-engaging wheels 14. Each of wheels 14 having a locking lever 16. This permits base 12 to be wheeled into position with wheels 14 turning freely as illustrated in FIG. 1. Locking lever 16 is then brought into contact with wheels 14 to preclude further rotation of wheels 14, as illustrated in FIG. 2. An elongate support member 18 is provided having a first end 20 and a second end 22. Second end 22 is secured to base 12. First end 20 extends substantially vertically from base 12. An upper or first arm 24 is provided which is movable axially along support member 18. First arm 24 is locked in a selected position to support member 18 by a locking assembly 26 which includes a locking/release lever 28 and an incremental adjustment lever 30. The manner of operation of locking/release lever 28 and incremental adjustment lever 30 are shown in greater detail in FIGS. 6 and 7. Referring to FIG. 6, locking/release lever 28 is pivotally mounted to first arm 24 and has an aperture 29 through which elongate support member 18 passes. Locking/release lever 28 is biased into an inclined position relative to elongate support member 18 by a biasing spring 31. As long as locking/release lever 28 is maintained in an inclined position, elongate support member 18 binds or jams within aperture 29. If a pressure is exerted upon locking/release lever 28 to compress biasing spring 31, locking/release lever 28 is able to move to a position substantially perpendicular to elongate support member 18. When locking/release lever 28 is in a substantially perpendicular position, elongate support member 18 is able to move freely through aperture 29. Referring to FIGS. 6 and 7, incremental adjustment lever 30 is pivotally mounted to a housing 33. Secured to incremental adjustment lever 30 is a gripping plate 35 with an aperture 37 through which elongate support member 18 extends. Gripping plate 35 is biased by a biasing spring 39 into a position substantially perpendicular to elongate support member 18. In this substantially perpendicular position, elongate support member 18 slides freely through aperture 37. However, when pressure is applied to incremental adjustment lever 30, the biasing force of biasing spring 39 is over come enabling gripping plate 35 to move to an inclined position in which elongate support member 18 binds within aperture 37. With continued application of pressure, gripping plate 35 engages elongate support member 18 to move first arm 24 a fraction of an inch downward. The downward force temporarily compresses biasing spring 31 of locking/release lever 28, so that incremental adjustment lever 30 does not have to work against locking/release lever 28. It therefore follows that there is provided: means, associated with the upper arm, for disengagably locking it to the support member to prevent sliding movement thereal-ong; and means, also associated with the upper arm, for temporarily disengaging the locking means and incrementally advancing the upper arm downwardly along the support member. A lower or second arm 32 is provided which is also movable axially upwardly along support member 18. Second arm 32 is locked in a selected position to support member 18 by a locking assembly 34 which includes a locking/release lever 36 and an incremental adjustment lever 38. In all respects locking assembly 34 is identical to locking assembly 26, previously described. Thus there is also provided: means, associated with the lower arm, for disengagably locking it to the support member to prevent sliding movement therealong; and means, also associated with the lower arm, for temporarily disengaging the locking means and incrementally advancing the lower arm upwardly along the support member. A haemostatic compression member 40 is secured to first arm 24. The member 40 extends downwardly or is oriented toward second arm 32. Referring to FIG. 5 haemostatic compression member 40 is has a generally arcuate contact face and a peripheral edge 42 with a slot 44 extending in from peripheral edge 42. Referring to FIGS. 2 and 3, a gauge 46 for measuring compressive force is coupled with haemostatic compression member 40. This enables a reading of a compressive force exerted by haemostatic compression member 40 to be obtained. Referring to FIG. 4, the operation of gauge 46 is further illustrated. Gauge 46 includes a shaft 48 which has a first end 50 and a second end 52. Haemostatic compression member 40 is mounted on first end 50 of shaft 48. Second end 52 is telescopically received in a bore 54 of a vertically aligned rack 56 and engages a spring 58. Rack 56 extends into a gauge housing 60 and engages a pinion gear 62. The rotation of pinion gear 62 is resisted by a spring 64 which has a known resistance. The resulting reading is reflected on dial 66. Second arm 32 has a contact member 68.

The use of haemostatic compression apparatus 10 in accordance with the preferred method will now be described in relation to FIGS. 1 through 6. Firstly, provide an haemostatic compression apparatus, preferably as described in relation to haemostatic compression apparatus 10. Secondly, referring to FIG. 2, place second end 22 of support member 18 on a floor 70 immediately adjacent to a bed 72 containing a patient 74 and move second arm 32 axially along support member 18 until contact member 68 of second arm 32 engages an underside 76 of bed 72. In the preferred embodiment, second end 22 of support member 18 includes base 12 having a plurality of floor-engaging wheels 14. Base 12 is wheeled into position with wheels 14 turning freely as illustrated in FIG. 1. Locking lever 16 is then brought into contact with wheels 14 to preclude further rotation of wheels 14, as illustrated in FIG. 2. Second arm 32 is positioned by manipulating locking/release lever 36 and an incremental adjustment lever 38 of locking assembly 34. Locking/release lever 36 enables second arm 32 to be moved rapidly along support member 18 toward underside 76 of bed 72. Incremental adjustment lever 38 allows additional incremental pressure to be applied to bring contact member 68 into firm contact with underside 76 of bed 72. Thirdly, move first arm 24 axially along support member 18 until haemostatic compression member 40 engages patient 74 to apply a compression force. In the preferred embodiment, as described above, this is done by manipulating first locking/release lever 28 and then incremental adjustment lever 30 of locking assembly 26. Locking/release lever 28 enables first arm 24 to be moved rapidly along support member 18 toward patient 74. Haemostatic compression member 40 is rotated to ensure slot 44 lies at right angles across both an artery providing blood from the patient's heart to a limb and a vein through which blood from the limb returns to the heart. Incremental adjustment lever 30 then allows incremental pressure to be applied to bring haemostatic compression member 40 into firm contact with patient 74 to stop bleeding from the artery. The amount of pressure exerted by haemostatic compression member 40 can be carefully monitored with regard to gauge 46.

It will be apparent to one skilled in the art that modifications may be made to the illustrated embodiment without departing from the spirit and scope of the invention as hereinafter defined in the claims. In particular, it will be apparent to one skilled in the art that the teachings of the method can be applied using a simplified version of haemostatic compression apparatus 10.

The embodiments of the invention in which an exclusive property of privileged is claimed are defined as follows:

1. A method for haemostatic compression, comprising the steps of:

firstly, providing an elongate support member having a first end and a second end, a first arm movable axially along the support member, a second arm movable axially along the support member, a haemostatic compression member secured to the first arm oriented toward the second arm;

secondly, placing the second end of the support member on a floor immediately adjacent to a bed containing a patient and moving the second arm axially along the support member until the second arm engages an underside of the bed;

thirdly, moving the first arm axially along the support member until the haemostatic compression member engages the patient and applies a compression force.

2. A floor-supported haemostatic compression apparatus for use with a patient supported on a generally horizontally extending bed, comprising:

a wheel-supported base;

a support member extending upwardly from the base and being of sufficient length to extend above the patient;

upper and lower arms, each having inner and outer ends and being mounted at its inner end to the support member so as to be freely slidable therealong;

the upper arm extending horizontally and having sufficient length so that its outer end may be positioned over the patient when the support member is adjacent the bed, said upper arm carrying a downwardly extending, haemostatic compression member at its outer end;

the lower arm being generally L-shaped and comprising a horizontally extending first section and an upwardly extending second section, the first section having sufficient length so that the second section may be positioned beneath the patient, the second section having sufficient length to engage the underside of the bed while providing clearance of the first section relative to the bed;

means, associated with the upper arm, for disengagably locking it to the support member to prevent sliding movement therealong;

means, associated with the upper arm, for temporarily disengaging the upper arm locking means and incrementally advancing the upper arm downwardly along the support member; and means, associated with the lower arm, for disengagably locking it to the support member to prevent sliding movement therealong.

3. The apparatus as set forth in claim 2 comprising:

means, associated with the lower arm, for temporarily disengaging the lower arm locking means and incrementally advancing the lower arm upwardly along the support member.

\* \* \* \* \*